US00PP08872P

United States Patent [19]

Kordes

[11] Patent Number: Plant 8,872

[45] Date of Patent: Aug. 30, 1994

[54] SHRUB ROSE PLANT NAMED KORFULLWIND

[75] Inventor: Wilhelm Kordes, Sparrieshoop, Fed. Rep. of Germany

[73] Assignee: Bear Creek Gardens, Inc., Medford, Oreg.

[21] Appl. No.: 127,141

[22] Filed: Sep. 22, 1993

[51] Int. Cl.[5] ..... A01H 5/00

[52] U.S. Cl. ..... Plt./1

[58] Field of Search ..... Plt. 1, 26

*Primary Examiner*—Howard J. Locker

*Attorney, Agent, or Firm*—Klarquist Sparkman Campbell Leigh & Whinston

[57] ABSTRACT

Shrub rose plant having dark green, glossy, disease-resistant foliage; a compact spreading habit, rapid repeat blooming and attractive pink blooms in clusters.

1 Drawing Sheet

The present invention relates to a new and distinct variety of rose plant of the shrub class which was originated by me by crossing the variety KORweirim with the variety KORfalt.

The primary objective of this breeding was to produce a new rose variety having the vigor, health and ground covering habit of KORweirim and the larger flower and deep yellow flower color of KORfalt, along with its rapid reblooming ability. Except for the flower color, the objective was substantially achieved, along with other desirable improvements, as evidenced by the following unique combination of characteristics that are outstanding in the new variety and that distinguish it from its parents, as well as from all other varieties of which I am aware:

1. Dark green, glossy foliage;
2. Low growing, spreading habit of growth;
3. Rapid rebloom;
4. Resistance to most major rose diseases; and
5. Attractive pink flowers borne in clusters.

Asexual reproduction of this new variety by budding and softwood cuttings, as performed at Wasco, Calif., and Sparrieshoop, Germany, shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) Colour Chart, except where ordinary dictionary significance of color is indicated.

Parentage:

*Seed parent.*—KORweirim.

*Pollen parent.*—KORfalt.

Classification:

*Botanical.*—*Rosa hybrida.*

*Commercial.*—Shrub.

FLOWER

Observations made from specimens grown in a garden environment in Somis, Calif., and Sparrieshoop, Germany, from Mar. to Jul., 1993.

Blooming habit: Continuous.

Bud:

*Size.*—½ to ¾ inches in length when the petals start to unfurl.

*Form.*—Short, pointed ovoid.

*Color.*—When sepals first divide, bud color is Red Group 49A. When half blown, the upper and lower sides of the petals are Red Group 49B.

*Sepals.*—Color: Green Group 139B. Surface texture: Covered in fine hairs. There are three lightly appendaged sepals. There are two unappendaged sepals with hairy edge.

*Receptacle.*—Color: Green Group 141C. Shape: Apple. Size: Small (¼ inch×⅜ inch). Surface: Smooth.

*Peduncle.*—Length: Short (1½ inches). Surface: Glandular. Color: Medium green. Strength: Stiff, erect.

Bloom:

*Size.*—Medium to small. Average open size is 2½ to 3 inches in diameter.

*Borne.*—Several together in rounded to flat clusters of from 3 to as many as 15 flowers.

*Stems.*—Short (6 to 10 inches), strong.

*Form.*—When first open: High centered. Permanence: Flattens.

*Petalage.*—Number of petals under normal conditions: 15 to 20.

*Color.*—The upper and reverse sides of the petals are Red Group 49B. At the base of each petal is a small yellow half moon (Yellow Group 4B) at the point of attachment. The major color on the upper side is Red Group 49B.

*Variegations.*—None.

*Discoloration.*—The general tonality at the end of the first and third days: No change. By the end of the fourth day under bright sun, there is a gradual fading to Red Group 49C and Red Group 49D.

*Fragrance.*—Slight.

Petals:

*Texture.*—Thick.

*Shape.*—Oval, notched.
*Form.*—Flat.
*Arrangement.*—Imbricated, with no petaloids in the center.
*Persistence.*—Drop off cleanly.
*Lastingness.*—On the plant: Short (4 to 5 days). As a cut flower: Short (4 to 5 days).

Reproductive parts:
*Anthers.*—Size: Medium. Quantity: Many. Color: Yellow. Arrangement: Regular around the styles.
*Filaments.*—Color: Greenish white.
*Pollen.*—Color: Gold-yellow.
*Styles.*—Color: Light pink.
*Stigmas.*—Color: Greenish white.

Form: Bush.

Growth: Vigorous, branching, sprawling, compact. Average height in California after 2 years with no pruning is 3 feet. The average width in California after 2 years with no pruning is 3 feet.

Foliage:
*Number of leaflets on normal mid-stem leaves.*—5 to 7.
*Size.*—Small (4 inches×2½ inches).
*Quantity.*—Abundant.
*Color.*—New foliage: Greyish-Red Group 181A rapidly turning to Yellow-Green Group 144A. Old foliage: Green Group 137A.

Leaflets:
*Shape.*—Pointed oval.
*Texture.*—Upper side: Leathery, glossy.

*Edge.*—Serrated.
*Serration.*—Single, small.
*Petiole rachis.*—Color: Reddish when young, then green.
*Petiole underside.*—Smooth with occasional prickles and glands.
*Stipules.*—Short (⅜ inch) and bearded.
*Disease resistance.*—Resistant to mildew, blackspot and rust under normal growing conditions at Somis, Calif., and Sparrieshoop, Germany.

Wood:
*New wood.*—Color: Light green. Bark: Smooth.
*Old wood.*—Color: Green. Bark: Smooth.

Prickles:
*Quantity.*—Ordinary on main canes from base. Ordinary on laterals from main canes.
*Forms.*—Short (¼ inch), hooked slightly downward.
*Color when young.*—Green.

Small prickles:
*Quantity.*—On main stalks: None. On laterals: None.

I claim:

1. A new and distinct variety of rose plant of the shrub class, substantially as herein shown and described, characterized particularly as to novelty by the unique combination of its dark green, glossy, disease-resistant foliage; its compact spreading habit of growth; its rapid repeat bloom and its attractive pink blooms borne in clusters.

* * * * *

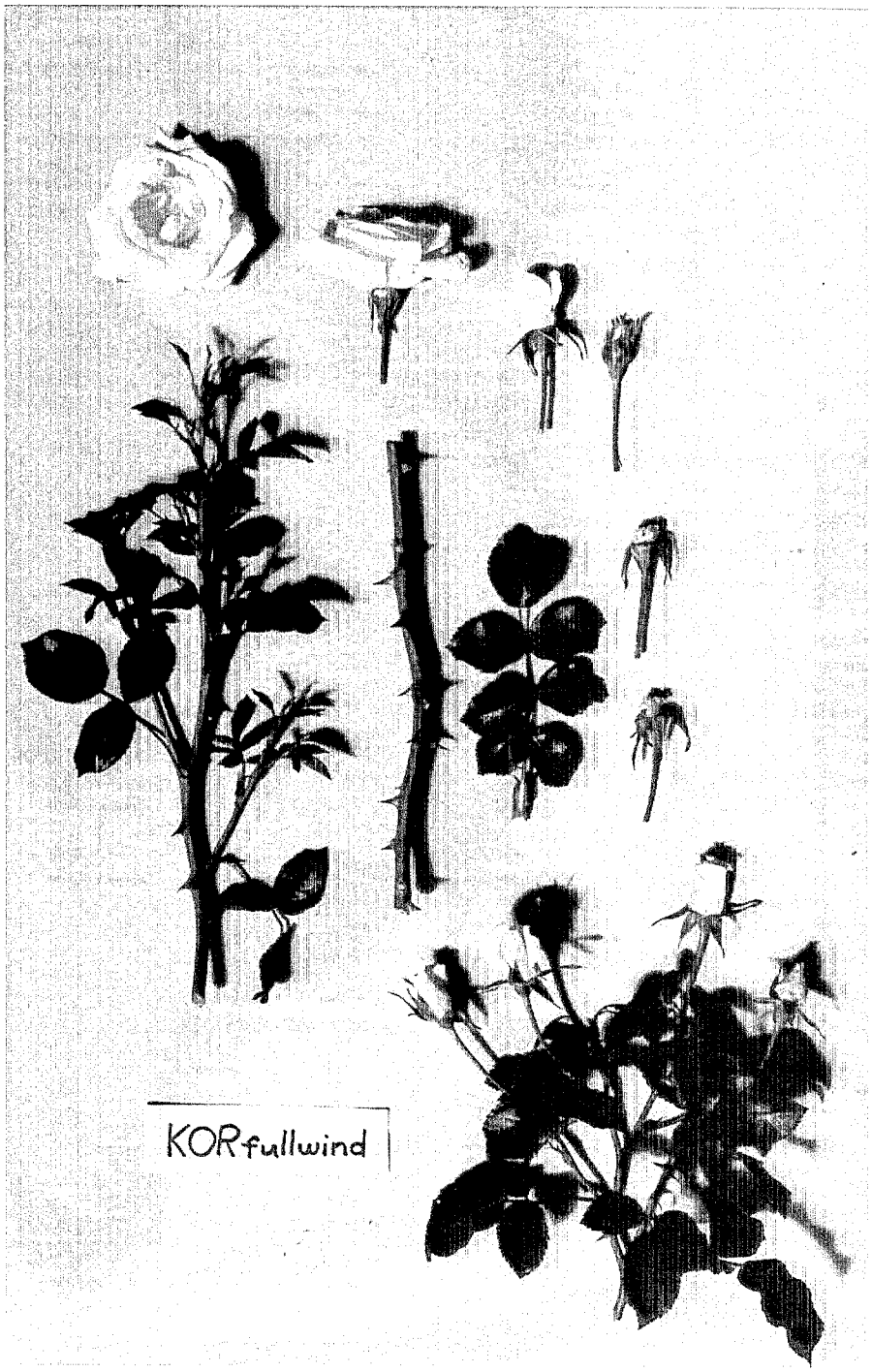
KORfullwind